United States Patent [19]
Scopelianos et al.

[11] Patent Number: 6,031,018
[45] Date of Patent: Feb. 29, 2000

[54] SOLVENTLESS TIPPING OF BRAIDED SURGICAL LIGATURE

[75] Inventors: Angelo G. Scopelianos; Rao S. Bezwada, both of Whitehouse Station, N.J.

[73] Assignee: Ethicon, Inc., Somerville, N.J.

[21] Appl. No.: 08/980,540

[22] Filed: Dec. 1, 1997

Related U.S. Application Data

[63] Continuation of application No. 08/431,094, Apr. 28, 1995, abandoned.

[51] Int. Cl.$^7$ .............................. B05D 1/36; A61B 17/04
[52] U.S. Cl. ...................... 523/105; 524/599; 528/354; 606/231; 427/2.31
[58] Field of Search .................. 523/105; 524/599; 528/354; 606/231; 427/2.31

[56] References Cited

U.S. PATENT DOCUMENTS

| | | | |
|---|---|---|---|
| 2,240,330 | 4/1941 | Flagg et al. | 128/339 |
| 3,736,646 | 6/1973 | Schmitt et al. | 29/458 |
| 3,890,975 | 6/1975 | McGregor | 128/339 |
| 3,918,455 | 11/1975 | Coplan | 128/339 |
| 3,981,307 | 9/1976 | Borysko | 128/339 |
| 4,127,133 | 11/1978 | Martinez | 128/339 |
| 4,595,713 | 6/1986 | St. John | 523/105 |
| 4,624,256 | 11/1986 | Messier et al. | 128/335.5 |
| 4,664,655 | 5/1987 | Orentreich et al. | 604/232 |
| 4,758,234 | 7/1988 | Orentreich et al. | 604/232 |
| 4,791,929 | 12/1988 | Jarret et al. | 128/335 |
| 4,803,075 | 2/1989 | Wallace et al. | 424/423 |
| 4,805,292 | 2/1989 | Noguchi | 29/445 |
| 4,832,025 | 4/1989 | Coates | 128/335.5 |
| 4,938,763 | 7/1990 | Dunn et al. | 604/891.1 |
| 5,204,382 | 4/1993 | Wallace et al. | 523/115 |
| 5,250,247 | 10/1993 | Chesterfield et al. | 264/157 |
| 5,259,846 | 11/1993 | Granger et al. | 606/224 |
| 5,269,808 | 12/1993 | Proto et al. | 606/228 |
| 5,278,201 | 1/1994 | Dunn et al. | 523/113 |
| 5,278,202 | 1/1994 | Dunn et al. | 523/113 |

FOREIGN PATENT DOCUMENTS

| | | | |
|---|---|---|---|
| 1009532 | 5/1977 | Canada | 128/123 |
| 2026358 | 5/1991 | Canada | D02J 13/00 |
| 0376656 | 7/1990 | European Pat. Off. | A61L 17/00 |
| 0485215 | 5/1992 | European Pat. Off. | A61L 17/00 |

OTHER PUBLICATIONS

Chem. Abst. vol. 109, 1938: 156306j Bioabsorbable Coating for Suturs and Ligatures Peter Kendrick Jarrett, et al.

Chem. Abst. vol. 110, 1989 110: 237192s Caprolactone block copolymers as coatings for surgical articles. Peter Kendrick jarrett, et al.

Chem. Abst. vol. 111, 1989: 84169h Bioabsorbable Caprolactone Copolymer Coating for a Surgical Article Peter Kendrick Jarrett, et al.

Chem. Abst. vol. 113, 1990 29325x Sutures coated with esters, waxes, and/or polymers, Tatsuya Kawai, et al.

Chem. Abst. vol. 115, 1991 57259p Copolymers of e–caprolactone, glycolide and glycolie acid for surgical sturues coatings. Rao S. Bezwada, et al.

Chem. Abst. 115: 189847p Bioabsorbable copolymers of polyalkylnene carbonate–dioxanone for sturues and coatings Rao S. Bezwada, et al.

Chem. Abst. vol. 85, 1976 182436g Absorbable preparation and surgical suture material coated with it. Frank Mattei.

Chem. Abst. vol. 93, 1980 173783f Absorbable Coating Composition for Sutures Frank V. Mattei.

Chem. Abst. vol. 89, 1978 169123r Synthetic Absorbable Multifilament Suture Material with Improved Knotting Properties Ethicon, Inc.

Chem. Abst. vol. 117, 1992, 118551t Suture Coated with a Polymeric Compositions Rao S. Bezwada, et al.

Chem. Abst. vol. 106, 1987 182724b Caprolactone Polymers for Suture Coating Kenneth A. Messier, et al.

Chem. Abst. vol. 117, 1992 178362s Absorbable Coating Compositions, Coated Sutures and Method of Preparation Kaplan, Donald S., et al.

Chem. Abst. vol. 120, 1994 116889x Absorbable Coating Composition and Sutured Coated Therewith Mathew E. Hermes, et al.

Chem. Abst.121:42817u Surgical Filament, Shinoda, Hosei, et al.

Chem. Abst. vol. 120, 1994 200368j Bioabsorption of poly–e–caprolactone and copolymer of 3–caprolactone and L–lactide Teruo, Matsui, et al.

Chem. Abst. vol. 119, 1993 256574v Block Copolymers with reduced Friction for Articles in Contact with Human or Animal Tissues Peter K. Jarrett, et al.

Chem. Abst. vol. 118, 1993 154504j Hydrolytic Degradation and Morphologic Study of poly–p–dioxanone Hu Ling Lin, et al.

Chem. Abst. vol. 117, 1992 239885p Preparation of Medical Suture with Acylamino Acid Coatings; Hosei Shinoda, et al.

Chem. Abst. vol. 117, 1992 198470d Characterization of Surgical Suture Materials Using Dynamic Mechanical Analysis Von Fraunhofer, J. A., et al.

Chem. Abst. vol. 114, 1991 69114e Blends of Polycarpolactone and Crystallization Modifiers for Coating Surgical Articles and As Controlled–Release Matrixes. James R. Olson.

Chem. Abst. vol. 111, 1989 219340e Glycolide/p–dioxanone Block Copolymers for Surgical Sutures Dennis D. Jamiolkowski, et al.

(List continued on next page.)

*Primary Examiner*—Andrew E. C. Merriam
*Attorney, Agent, or Firm*—Hal Brent Woodrow

[57] ABSTRACT

The present claims are directed to a tipped surgical suture and a solventless method for making a tipped suture comprising a suture coated with 6–30 weight percent, based on the total weight of the tipped region of the suture, of a bioresorbable aliphatic polyester copolymer which itself comprises from 70–100 mole % of e-caprolactone repeating units or from 80–100 mole % of trimethylene carbonate repeating units, the remainder of repeating units in the copolymer comprising a plurality of lactide, 1,4-dioxan-2-one, 1,4-dioxepan-2-one units.

13 Claims, No Drawings

OTHER PUBLICATIONS

Chem. Abst. vol. 110, 1989 199139v In Vitro and In Vivo Degradation of poly(L–lactide) Braided Multifilament Yarns Brian C. Benicewicz, et al.

Chem. Abst., 1986 193157d Knot Stability and Tensile Strength of An Absorbable Suture Material I. K. Stone, et al.

Chem. Abst. 104:10661w Dry Coating of Surgical Filaments Donald W. Regula, et al.

Chem. Abst. vol. 96, 1982 223183v Recently Developed Surgical Threads Hiroyoshi Kobayashi.

SOLVENTLESS TIPPING OF BRAIDED SURGICAL LIGATURE

FIELD OF THE INVENTION

This invention is a continuation of Ser. No. 08/431,094, filed Apr. 28, 1995, now abandoned and relates to surgical ligature and processes for manufacturing said surgical ligature, more specifically, this invention relates to the solventless tipping of surgical sutures with a bioabsorbable polymer.

BACKGROUND OF THE INVENTION

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acid.

One typical method for securing a suture to a needle involves providing a cylindrical recess in the shank end of a needle and securing a suture therein. For example, U.S. Pat. No. 2,928,395 teaches the addition of an adhesive material to such a substantially cylindrical recess to secure the suture therein. Additional methods for bonding a suture within a needle bore are described in U.S. Pat. No. 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out value of 3 to 26 ounces. Martinez U.S. Pat. No. 4,127,133 also discloses the use of wax as a bonding agent for controlled release needles. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630, 3,926,194; 3,943,933; 3,981,307 and 4,124,027.

Another method for attaching a suture to a needle involves the use of tubing which is secured to the shank end of the needle and to the suture. For example, U.S. Pat. No. 1,613,206 describes the use of a tubing (preferably silver), which is secured to the shank end of a needle and to a ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are reasonably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needled attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330 1,981,651 (needle and tubing screw threaded), 1,960,117, and 1,591,021.

In addition to the needle-suture constructions of the afore described pull-out variety, it is known from U.S. Pat. No. 4,805,292 to provide a needle-suture combination in which a suture cutting edge is formed at the shank end of the needle. However, the combined needle-suture device of U.S. Pat. No. 4,805,292, like others described above, possesses a suture tip-receiving axial bore, or recess, formed in the butt end of the needle and as such is subject to the disadvantages recounted above which are associated with a needle possessing an axial bore.

Insertion of sutures into a hole, recess, or tube for attachment to surgical needles presents problems peculiar to suture needle combinations. Braided multifilament sutures in particular are difficult to inset into the very small aperture of a surgical needle; unless modified, they are too limp for the suture tip to be controlled for insertion and they have a tendency to "broom", i.e., the filaments have a tendency to flare out at the cut end so that the diameter of the cut end of the suture exceeds the diameter of the hole in the needle. Various techniques have been employed to modify sutures to overcome the problems of limpness and brooming. One known method employs a tipping agent, which is a material used to coat the suture to stiffen the filaments and adhere them together.

Typically, a suture to be tipped is first placed under tension to reduce slack so that the suture may be maintained in a predetermined position on a frame or rack or other suture holding device. Optionally, the tension may be such as to reduce the diameter of the suture. See Canadian Pat. No. 1,009,532. The suture is then dipped into the tipping solution and allowed to dry while under tension. The sutures are then dried, such as by being warmed in a drying oven at about 225° F. for about 10 minutes. After drying the sutures can be cut and released from tension. The process results in a tipped end on each side of a cut. Where tension has optionally been employed to reduce the suture diameter, release of said tension will allow the suture to expand to its original diameter except at the tipped end portion. This can facilitate insertion of the end into a needle.

Tipping agents are dissolved in solvents to form dipping solutions. By way of example, Mariotte mixture is a dipping solution comprising nylon dissolved in isopropyl alcohol. Other polymers and solvents may also be used. Gould mixture is a dipping solution comprising nylon dissolved in methanol. At least one major manufacturer of surgical needles recommends use of Mariotte mixture or Gould mixture for tipping sutures. A multitude of other tipping agents, including a polymer and solvent, have been proposed. For example, McGregor U.S. Pat. No. 3,890,975 discloses coating the suture with a binding resin or adhesive.

The composition may be any non-toxic adhesive composition, either organic, inorganic or a hybrid. Suitable organic materials are such natural products as starch, dextrin, asphalt, animal and vegetable proteins, natural rubber, shellac, semi-synthetic products such a cellulose nitrate and the other cellulosics, polyamides derived from dimer acids, castor-oil based polyurethanes; such well-known synthetic resins as vinyl-type addition polymers, both resins and elastomers; polyvinyl acetate, polyvinyl alcohol, acrylics, unsaturated polyesters, butadiene/acrylonitrile, butadiene/styrene, neoprene, butyl rubber, polyisobutylene; and polymers formed by condensation and other step-wise mechanisms, i.e. epoxies, polyurethanes, polysulfide rubbers, and the reaction products of formaldehyde with phenol, resorcinol, urea and melamine. McGregor states that particular preferred bonding compositions are epoxide resins and polyester resins.

Schmitt U.S. Pat. No. , 3,736,546, discloses that it is known to tip braided sutures by dipping the end of the suture in a plastic such as a solution of nylon in isopropyl alcohol. Schmitt suggests that for absorbable sutures an absorbable tipping agent is desirable, and proposes that a copolymer of lactic and glycol acid dissolved in a suitable organic solvent, such as xylene or toluene, be applied to tip the suture.

Nichols U.S. Pat. No. 2,734,506 discloses a tipping solution of polymers of methacrylic acid esters in an organic solvent such as toluene, xylene acetone, ethyl acetate, methethyl ketone, or naphtha.

Shepherd et al. U.S. Pat. No. 3,849,185 discloses the use of an acrylic casting syrup as a tipping agent, the syrup being fully polymerized after being applied to the suture.

In addition, paraffin/hexane solution (10% paraffin) has been used as a suture coating agent as well as ArroChem (TM), a nylon resin plus methanol composition manufactured by ArroChem, Inc. of 201 Westland Farm Road, Mt. Holly, N.C. 28120, and SILASTIC (TM) Medical Adhesive (a silicon elastomer composition manufactured by Dow Corning Co.).

Although tipped sutures prepared in accordance with the above procedures may have been used successfully, there are several drawbacks with the use of tipping solutions. The main problems related to tipping consistency and process control. Non-uniform solvent evaporation, which may be caused by variants in the solvent, oven temperature and heating time can result in inconsistent tipping. Furthermore, the dried residue of polymer left after evaporation can flake off or develop cracks. Additionally, most tipping solvents used in tipping solutions are hazardous and presents significant handling and disposal problems.

Another method for tipping sutures is to heat treat the suture tip. Since the 1970's braided thermoplastic sutures have been tipped by placing the end of a suture in a heated die to consolidate the end and form a shaped tip that was suitable for insertion into a needle. The die could be heated with an electric resistance heater or an ultrasonic generator. Sutures can also be tipped by contacting a heated surface to a tensioned length of suture to form a stiffened region which will be subsequently cut to form two tips. Recently, Coates described a variation on this approach in U.S. Pat. Nos. 4,832,025, 5,226,336, and 4,806,737, which consisted of heating a tensioned length of suture in a radiantly heated tunnel followed by cutting the heat treated length of suture to form two tips. Sutures can also be heat tipped by placing a thermoplastic suture on a rack or frame under tension and dipping the portion to be tipped into a hot inert fluid. The portion of the suture inserted into the inert fluid will be heat set or drawn (depending on the suture material, tension, the temperature of the fluid and the duration of the exposure to the heated fluid) and thereby stiffened. The suture may be removed from the rack or frame and the stiffened portion can be subsequently cut to form one or more suture tips. Unfortunately, using heat to melt a region of the suture may weaken the suture if not carefully controlled.

Thus, it would be a significant contribution to the art to tip sutures without using solvents or exposing the suture to high temperatures. It is, therefore, an object of the present invention to provide a process for tipping braided surgical ligatures on sutures that do not require the use of tipping solvents or high temperatures.

SUMMARY OF THE INVENTION

We have discovered a surgical suture tipped with an aliphatic polyester comprising a suture that for a length of less than forty millimeters from at least one end of the suture has been tipped with an aliphatic polyester, provided that the aliphatic polyester is not a copolymer of glycolic acid and lactic acid, wherein the aliphatic polyester is provided in an amount sufficient to stiffen the suture for insetion into a surgical device.

In another embodiment of the present invention we have also discovered a process for tipping a surgical suture in the substantial absence of an organic solvent with a crystalline aliphatic polyester comprising tipping a portion of a suture with a quantity of melted aliphatic polyester; and cooling the portion of the suture that has been tipped.

DETAILED DESCRIPTION OF THE INVENTION

The present invention is generally directed to tipping surgical sutures with crystalline aliphatic polyesters in order to stiffen the sutures tip and for multifilament sutures to prevent brooming. Tipping the suture facilitates insert-on of the suture tip into an opening for attachment to needled or other surgical devices.

The present invention is primarily directed to the treatment of braided surgical sutures. The term "braid" means a substantially symmetrical strand formed by crossing a number (at least three) of individual strands composed of one or more filaments diagonally in such manner that each strand passes alternatively over and under one or more of the others. The braid may be of traditional tubular braid construction or spiroid braid construction and may include a core section composed of one or more filaments around which the braid is externally fabricated.

The braided suture can be fabricated from a wide variety of natural and synthetic fibrous materials such as any of those heretofore disclosed for the construction of sutures. Such materials include non-absorbable as well as partially and fully bio-absorbable (i.e., resorbable) natural synthetic fiber-forming polymers. Non-absorbable materials which are suitable for fabricating braided sutures include silk, polyamides, polyesters such as polyethylene terephthalate, polyacrylonitrile, polyethylene, polypropylene, silk cotton, linen etc. Carbon fibers, steel fibers and other biologically acceptable inorganic fibrous materials can also be employed. Bio-absorbable sutures may be fabricated from a natural collagenous material or synthetic resins including those derived from glycolic acid, glycolide, lactic acid, lactide, dioxanone, polycaprolactone, epsilon-caprolactone, trimethylene carbonate, etc., and various combinations of these and related monomers. Sutures prepared from resins of this type are known in the art.

Braided multifilament sutures typically are coated with 1 to 5 weight percent of one or more coating compositions to improve functional properties such as surface lubricity and knot tie-down behavior. A variety of suture coating compositions proposed for either or both of these purposes are well known in the art, e.g., those disclosed in U.S. Pat. Nos. 4,994,074, 4,791,929; 4,624,256; 4,185,637; 3,942,532, and European Patent Application 610,086 and 376,656.

The crystalline aliphatic polyester that are suitable for use as tipping agents are polymers that are solids at room temperature. The aliphatic polyester of this invention are generally characterized as being solids at room temperature (25° C.) and preferably for some applications will be solids at body temperature (37° C.). Suitable bioabsorbable aliphatic polyester include solid homopolymers poly($\epsilon$-caprolactone), poly(p-dioxanone), or poly(trimethylene carbonate) and copolymers of $\epsilon$-caprolactone and trimethylene carbonate. Copolymers of $\epsilon$-caprolactone should be composed of from about 100 mole percent to about 70 mole percent and preferably from 95 mole percent to 85 mole percent of $\epsilon$-caprolactone repeating units with the remainder of the polymer being a plurality of second lactone repeating units. The second lactone repeating units will be selected from the group consisting of glycolide repeating units, lactide repeating units, 1,4-dioxanone repeating units, 1,4-dioxepan-2-one repeating units, 1,5-dioxepan-2-one repeating units, trimethylene carbonate repeating units, and combinations thereof. Preferred are copolymers of $\epsilon$-caprolactone that are semicrystalline solids at body temperature. The solid polymers of trimethylene carbonate should be composed of from in the range of from about 1 to about 20 mole percent or from about 100 to about 80 mole percent of trimethylene carbonate with the remainder of the copolymer being composed of a plurality of lactone repeating units selected from the group consisting of glycolide repeating units, lactide repeating units, p-dioxanone repeating units, $\epsilon$-caprolactone repeating units, and combinations thereof. It is preferred for the trimethylene carbonate copolymers to have crystalline regions formed by the second lactone repeating units wherein the crystalline regions provide at least 5 percent crystallinity to the final copolymer. The solid polymers may be linear, branched, or star branched; block copolymers or terpolymers; segmented block copolymers or terpolymers.

The most preferred polymers for use as the particulate material are crystalline polymers selected from the group consisting of poly($\epsilon$-caprolactone), poly($\epsilon$-caprolactone-co-trimethylene carbonate), poly($\epsilon$-caprolactone-co-lactide), and poly($\epsilon$-caprolactone-co-p-dioxanone). The mole percent of $\epsilon$-caprolactone repeating units in these polymers should be in the range of from 100 to about 80 mole percent and preferably in the range of from 95 to 85 mole percent.

The polymers used as the particulate material should have an inherent viscosity, as determined at a concentration of 0.1 g/dL in hexafluoroisopropanol (HFIP) at 25° C., in the range of from about 0.1 dL/g to about 1.0 dL/g, preferably from about 0.1 dL/g to about 0.8 dL/g, and most preferably from 0.15 dL/g to 0.5 dL/g. A polymer with an inherent viscosity below 0.1 dL/g may fail to crystallize at room temperature, and a polymer with an inherent viscosity above 1.0 dL/g may make the tipping agent too viscous to be easily administered.

These polymers may be formed in a ring opening polymerization reaction. Currently, it is preferred to initiate the ring opening polymerization with high boiling alcohols (such as 1-dodecanol), diols and triols (such as 1,2-propanediol, 1,3-propanediol, diethylene glycol, or glycerol) or polyols (such as polyethyleneglycols, polypropyleneglycols and polyethylenepropyleneglycols). Additionally, some of the monomers described above may be replaced by an equivalent amount of the corresponding acid (such as the substitution of two equivalents of glycolic acid for glycolide or two equivalents of L-lactic acid for L-lactide).

The polymers of the aliphatic ester can be prepared by polymerizing the desired proportions of one or more aliphatic esters in the presence of an organometallic catalyst and an initiator at elevated temperatures. The organometallic catalyst is preferably a tin-based catalyst, e.g. stannous octoate, and is present in the monomer mixture at a mole ratio of monomer to catalyst ranging from about 15,000 to 80,000/l. The initiator is typically an alkanol, a glycol, a hydroxyacid, or an amine, and is present in the monomer mixture at a mole ratio of monomer to initiator ranging from about 100 to 5000/l. The polymerization is typically carried out at a temperature range from 80 to 220° C., preferably 160–190° C., until the desired molecular weight and viscosity are achieved.

The crystalline aliphatic polyester tipping agent is then heated to its melting point. Generally, the melted aliphatic polyester will have a viscosity in the range of from about 75 cps to about 2,000 cps at the temperature at which the aliphatic polyester is applied to the suture. The aliphatic polyester may be contacted with the surgical suture in a variety of ways substantially in the absence of a solvent such as by dipping, spraying (such as with an air brush) or brushing. The method of contacting the suture with the melted aliphatic ester should facilitate the penetration of the melted polyester into the center or core of the suture. The aliphatic polyester should penetrate uniformly through the suture so that during the swaging of the needle around the suture tip, the tip will not collapse inwardly thereby substantially reducing the pull out strength of the suture from the needle (i.e. allowing the suture to be too easily removed from the needle). Generally, the aliphatic polyester should be contacted with the suture at a temperature below the melting point or degradation temperature of the suture material, preferably 50° C. below the melting point or degradation temperature and most preferably 100° C. below the melting point or degradation temperature of the suture material. The suture may be placed under tension while the aliphatic polyester is applied to decrease the diameter of the suture in the tipped segment. For example, if the suture is wound around a rack under tension and partially dipped into melted aliphatic polyester, the melted polyester preferably would have a viscosity in the range of from about 75 cps to about 150 cps at a temperature 100° C. below the melting temperature of the suture material.

The aliphatic polyester after contacting the suture upon cooling will solidify and crystallize stiffening the tipped segment of the suture and holding together the individual filaments to prevent brooming. The amount of aliphatic polyester applied to tip the surgical suture will generally be an amount sufficient to stiffen the surgical suture sufficiently so that it may be inserted into an opening to attach the suture to a needled or surgical device. Preferably, the bending rigidity of the suture tip should be in the range of from about 0.2 to about 2.0 gram force.cm$^2$ per suture (Kawabata Pure Bending Tester KEF-FB-2). Generally, the amount of aliphatic ester on the tipped segment of the suture will be in the range of from about 1 to about 30 weight percent of the total weight of the tipped segment, preferably in the range of from about 6 to about 30 weight percent and most preferably in the range of form about 11 to 20 weight percent.

The tipped segment may be cut to form at least one tip for insertion into an opening such as the end of a surgical needle. Two tips may be formed by cutting a tipped portion in two pieces. The tipped portion may be cut by any suitable means such as a blade moving transverse to the direction of the tipped segment. Preferably, the tipped segments will cut in a semi-circular guillotine blade to avoid flattening the end of the tipped segment.

The tipped end may be inserted into a needle with a barrel end having an axial aperture or a channel. The tipped end of the suture is inserted into the aperture and the end of the needle may then be swaged, crimped or otherwise constricted to grip and hold the suture, either permanently or with a pull-out force defined by the U.S.P.

The following non-limiting examples are provided to further illustrate the practice of the present invention, however, many different variation of the present invention are possible without departing from the scope of the present invention.

EXAMPLE 1

Homopolymer of Caprolactone with Propylene Glycol an Initiator

A flame dried, 250 mL, round bottom single neck flask was charged with 114.14 gm (1.0 mole) of ε-caprolactone, 0.73 mL of propylene glycol (USP grade), and 0.101 mL of a 0.33 M stannous octoate solution in toluene. The flask was fitted with a flame dried mechanical stirrer. The reactor was purged with nitrogen three times before venting with nitrogen. The reaction mixture was heated to 160° C. and maintained at this temperature for about 18–20 hours. The copolymer had an inherent viscosity of 0.546 dL/g as determined at a concentration of 0.1 g/dL in hexafluoroisopropanol (HFIP) at 25° C.. The copolymer was a low melting solid (58–60° C. Fisher Johns). The mole ratio of polycaprolactone/ε-caprolactone was determined to be 99.75/6.25 by NMR.

EXAMPLE 2

Copolymer of Caprolactone/p-dioxanone at 95/5 Mole Initial with Propylene Glycol as an Initiator A flame dried, 250 mL, round bottom single neck flask was charged with 108.43 gm (0.95 mole) of ε-caprolactone, 5.10 gm (0.05 mole) p-dioxanone, 2.94 mL propylene glycol (USP), and 0.101 mL a 0.33 M of stannous octoate solution in toluene. The flask was fitted with a flame dried mechanical stirrer. The reactor was purged with nitrogen three times before venting with nitrogen. The reaction mixture was heated to 160° C. and maintained at this temperature for about 24 hours, and then the bath temperature was dropped to 100° C. and maintained at that temperature for 24 hours. The copolymer had an inherent viscosity of 0.29 dL/g as determined at a concentration of 0.1 g/dL in hexafluoroisopropanol (HFIP) at 25° C. The copolymer was a low melting solid (43–47° C. Fisher Johns). The mole ratio of polycaprolactone/poly(p-dioxanone) was found to be 95.1/4.9 by NMR.

EXAMPLE 3

Copolymer of Caprolactone/p-dioxanone at 90/10 Mole Initial with Propylene Glycol as an Initiator A flame dried, 250 mL, round bottom single neck flask was charged with 102.72 gm (0.90 mole) of ε-caprolactone, 10.21 gm (0.10 mole) p-dioxanone, 2.94 mL propylene glycol (USP), and 0.101 mL of a 0.33 M stannous octoate solution in toluene. The flask was fitted with a flame dried mechanical stirrer. The reactor was purged with nitrogen three times before venting with nitrogen. The reaction mixture was heated to 160° C. and maintained at this temperature for about 24 hours, and then the bath temperature was dropped to 100° C. and maintained there for 24 hours. The copolymer had an inherent viscosity of 0.23 dL/g as determined at a concentration of 0.1 g/dL in hexafluoroisopropanol (HFIP) at 25° C. The copolymer was a low melting solid (38–41° C. Fisher Johns). The mole ratio of polycaprolactone/poly(p-dioxanone) was found to be 90/10 by NMR.

EXAMPLE 4

Copolymer of Caprolactone/L(−)Lactide at 95/5 Mole Initial with Propylene Glycol as an Initiator A flame dried, 250 mL, round bottom single neck flask was charged with 108.43 gm (0.95 mole) of caprolactone, 7.20 gm (0.05 mole) L(−)lactide, 2.57 mL propylene glycol (USP), and 0.101 mL of a 0.33 M solution of stannous octoate in toluene. The flask was fitted with a flame dried mechanical stirrer. The reactor was purged with nitrogen three times before venting with nitrogen. The reaction mixture was heated to 160° C. and maintained at this temperature for about 18 hours. The copolymer had an inherent viscosity of 0.24 dL/g as determined at a concentration of 0.1 g/dL in hexafluoroisopropanol (HFIP) at 25° C. The copolymer was a low melting solid (45–47° C. Fisher Johns). The mole ratio of polycaprolactone/polylactide was found to be 98.8/1.2 by NMR.

EXAMPLE 5

Copolymer of Caprolactone/L(−)Lactide at 90/10 Mole Initial with Glycerol as an Initiator A flame dried, 250 mL, round bottom single neck flask was charged with 102.73 gm (0.90 mole) of caprolactone, 14.41 gm (0.05 mole) L(−)lactide, 1.82 mL glycerol (USP), and 0.101 mL of a 0.33 M stannous octoate solution in toluene). The flask was fitted with a flame dried mechanical stirrer. The reactor was purged with nitrogen three times before venting with nitrogen. The reaction mixture was heated to 160° C. and maintained at this temperature for about 18 hours. The copolymer was dried under vacuum (0.1 mm Hg) at 80° C. for about 28 hours to remove any unreacted monomer. The copolymer had an inherent viscosity of 0.30 dL/g as determined at a concentration of 0.1 g/dL in hexafluoroisopropanol (HFIP) at 25° C. The copolymer was a low melting solid (32–36° C. Fisher Johns). The mole ratio of polycaprolactone/polylactide was found to be 93.0/7.0 by NMR.

EXAMPLE 6

Copolymer of Caprolactone/L(−)Lactide at 90/10 Mole Initial with Propylene Glycol as an Initiator The procedure in Example 5 was substantially repeated, except that 2.57 mL propylene glycol was used instead of 1.82 mL of glycerol (distilled). The copolymer was isolated and characterized. The copolymer has an inherent viscosity of 0.28 dL/g as determined at a concentration of 0.1 g/dL in hexafluoroisopropanol (HFIP) at 25° C. The copolymer was a low melting solid (36–41° C. Fisher Johns). The mole ratio of polycaprolactone/polylactide was found to be 90.9/9.1 by NMR.

EXAMPLE 7

Pull-out Value Test of Surgical Sutures Tipped with a Bioabsorbable Polymer

Sixteen size 2-0 polyester sutures were dipped into melted polycaprolactone that had been prepared as described in Example 1. The tipped sutures were inserted into a CT-1 drilled needles with a hole diameter of 0.0175 inches (produced by Ethicon of Somerville, N.J.). If the tip of the suture had a droplet of solidified polycaprolactone on the end portion or the tip, the end portion of the tip was cut off before insertion into the drilled needle. The tips were inserted into the needles and the needles were swaged onto the tipped region of the sutures. The pull out values of the sutures were then determined by pull testing the sutures. The pull out values ranged from 2.0 lbs to 4.8 lbs. The sutures coated with less polycaprolactone on the tip had higher pull out values.

From this experimental work on tipping it is apparaent that by controlling the amount of bioabsorbable polymer deposited on the suture and the swaging process that the pull-out values of the suture can be easily varied to provide a suitable commercial suture or controlled release suture.

We claim:

1. A surgical suture tipped with an aliphatic polymer comprising a suture that for a length of less than forty millimeters from at least one end of the suture has been tipped with an aliphatic polymer to provide a tipped region wherein the aliphatic polymer constitutes in the range of from about 6 to about 30 weight percent of the total weight of the tipped region, provided that the aliphatic polymer is a crystalline aliphatic polymer selected from the group consisting of copolymers of $\epsilon$-caprolactone composed of from about 100 mole percent to about 70 mole percent of $\epsilon$-caprolactone repeating units with the remainder of the polymer being a plurality of second lactone repeating units selected from the group consisting of glycolide repeating units, lactide repeating units, 1,4-dioxan-2-one repeating units, 1,4-dioxepan-2-one repeating units, 1,5-dioxepan-2-one repeating units, trimethylene carbonate repeating units and combinations thereof and copolymers of trimethylene carbonate composed of from in the range of from about 100 to about 80 mole percent trimethylene carbonate with the remainder of the copolymer being composed of a plurality of lactone repeating units selected from the group consisting of glycolide repeating units, lactide repeating units, 1,4-dioxan-2-one repeating units and combinations thereof wherein the aliphatic polymer is a solid at body temperature and provide in an amount sufficient to stiffen the tipped region of the suture for insertion into an end of a needle.

2. The suture of claim 1 wherein the suture is a braided suture.

3. The suture of claim 1 wherein the aliphatic polymer has an inherent viscosity as determined in a 0.1 g/dL solution of hexafluoroisopropanol at 25° C. ranging from about 0.1 dL/g to about 1.0 dL/g.

4. The suture of claim 1 wherein a needle is attached to the end of the suture that has been tipped with the aliphatic polymer.

5. A process for tipping a surgical suture in the substantial absence of an organic solvent with a crystalline aliphatic polymer comprising tipping a portion of a suture for a length of less than forty millimeters from at least one end of the suture with a melted aliphatic polymer that is a solid at body temperature; and cooling the portion of the suture that has been tipped to form a tipped region wherein the aliphatic polymer constitutes in the range of from about 6 to about 30 weight percent of the total weight of the tipped region wherein the aliphatic polymer is a crystalline aliphatic polymer selected from the group consisting of copolymers of $\epsilon$-caprolactone composed of from about 100 mole percent to about 70 mole percent of $\epsilon$-caprolactone repeating units with the remainder of the polymer being a plurality of second lactone repeating units selected from the group consisting of glycolide repeating units, lactide repeating units, 1,4-dioxan-2-one repeating units, 1,4-dioxepan-2-one repeating units, 1,5-dioxepan-2-one repeating units, trimethylene carbonate repeating units and combinations thereof and copolymers of trimethylene carbonate composed of from in the range of from about 100 to about 80 mole percent trimethylene carbonate with the remainder of the copolymer being composed of a plurality of lactone repeating units selected from the group consisting of glycolide repeating units, lactide repeating units 1,4-dioxan-2-one repeating units and combinations thereof.

6. The process of claim 5 wherein the portion of the suture that has been tipped is cut to form at least one suture tip.

7. The process of claim 6 wherein a needle is attached the suture tip.

8. The process of claim 5 wherein the suture is a braided suture.

9. The process of claim 5 wherein the aliphatic polymer has an inherent viscosity as determined in a 0.1 g/dL solution of hexafluoroisopropanol at 25° C. ranging from about 0.1 dL/g to about 1.0 dL/g.

10. The surgical suture of claim 1 wherein the tipped region of the suture has a bending rigidity of in the range of from about 0.2 to about 2.0 gram force.cm$^2$.

11. The process of claim 7 wherein the tipped region of the suture is attached to a needle with an axial aperture by inserting the tipped region of the suture into the axial aperture and constricting a portion of the axial aperture of the needle about the tipped region.

12. The process of claim 7 wherein the tipped region of the suture is attached to a needle with a channel by inserting the tipped region of the suture into the channel and constricting a portion of the channel of the needle about the tipped region.

13. The process of claim 5 wherein the tipped region of the suture has a bending rigidity of in the range of from about 0.2 to about 2.0 gram force.cm$^2$.

* * * * *